United States Patent [19]
Matsushita et al.

[11] Patent Number: 6,084,059
[45] Date of Patent: Jul. 4, 2000

[54] PRODUCTION PROCESS FOR ORGANOMETALLIC FINE PARTICLE AND CATALYST FOR POLYMERIZATION

[75] Inventors: Teruki Matsushita, Suita; Hiroya Kobayashi, Minoo, both of Japan

[73] Assignee: Nippon Shokubai Co., Ltd., Osaka, Japan

[21] Appl. No.: 09/280,086

[22] Filed: Mar. 29, 1999

[30] Foreign Application Priority Data

Apr. 3, 1998 [JP] Japan ................................ 10-091118

[51] Int. Cl.[7] ................................................. C08G 59/68
[52] U.S. Cl. ........................ 528/414; 502/156; 502/513
[58] Field of Search ........................... 528/414; 502/156, 502/513

[56] References Cited

U.S. PATENT DOCUMENTS

| | | | |
|---|---|---|---|
| 2,971,988 | 2/1961 | Hill | 260/632 |
| 4,667,013 | 5/1987 | Reichle | 528/414 |
| 5,326,852 | 7/1994 | Fujikake et al. | 528/414 |

FOREIGN PATENT DOCUMENTS

| | | |
|---|---|---|
| 0239973 | 3/1987 | European Pat. Off. . |
| 457751 | 3/1970 | Japan . |
| 53-27319 | 8/1978 | Japan . |
| 62-232433 | 10/1987 | Japan . |
| 62-273227 | 11/1987 | Japan . |
| 02086843 | 3/1990 | Japan . |
| 517566 | 1/1993 | Japan . |
| 5310908 | 11/1993 | Japan . |
| 08059840 | 3/1996 | Japan . |
| 09278598 | 10/1997 | Japan . |

*Primary Examiner*—Samuel A. Acquah
*Attorney, Agent, or Firm*—Roylance, Abrams, Berdo & Goodman, L.L.P.

[57] ABSTRACT

The present invention provides: a production process for a polyalkylene oxide with fast polymerization reaction rate and good production efficiency; a catalyst for polymerization and a dispersion thereof which are effective for the above production process for a polymer such as polyalkylene oxide; and an organometallic fine particle and a production process therefor, which particle is, for example, useful as the above catalyst for polymerization. In a means therefor, a material such as an aliphatic polyol is reacted upon an organometallic compound in a micelle as the reaction field, thus preparing a hyperfine particle, which is used as a catalyst for polymerization of ionic-polymerizable monomers mainly including a cyclic ether.

11 Claims, No Drawings

1

PRODUCTION PROCESS FOR ORGANOMETALLIC FINE PARTICLE AND CATALYST FOR POLYMERIZATION

TECHNICAL FIELD

The present invention relates to an organometallic fine particle, a production process therefor, a catalyst for polymerization, a dispersion thereof, and a production process for a (poly)alkylene oxide, and in more detail, relates to: an organometallic fine particle effective for producing a high-molecular polymer or copolymer at a high reaction rate; a production process for the fine particle; a catalyst for polymerization comprising the fine particle; a dispersion of the catalyst; and a production process for a (poly)alkylene oxide using the catalyst.

BACKGROUND ART

Polymerization of such as alkylene oxide compounds to give high-molecular polymers and copolymers has been known for a long time, and the number of the bibliographies about this subject amounts to several hundred. The polymerization of the alkylene oxide is conventionally carried out using the wide range of catalysts as based on metal atoms which include oxides and/or hydroxides of transition metals such as iron and metals such as magnesium, aluminum, zinc, and calcium. U.S. Pat. No. 2,971,988 (issued Feb. 14, 1961) discloses an amide/metal alkoxide catalyst as based on calcium and reformed with ammonia. However, such a catalyst frequently leaves a formed polymer which has unpleasant smells of ammonia and amines, and those unpleasant smells are difficult to remove. Moreover, there are problems in that the operation of preparing the catalyst is complicated, and in that if no post-treatment such as heat-aging is performed, it is hard to obtain catalytic activity.

In addition, on the other hand, zinc catalysts are also researched. For example, JP-B-45-007751 and JP-B-53-027319 disclose that a product, as obtained by reacting a monohydric alcohol upon a product from a reaction between an organozinc compound and a polyhydric alcohol, or by reacting a polyhydric alcohol upon a product from a reaction between an organozinc compound and a monohydric alcohol, exhibits excellent catalytic activity to homopolymerization of an alkylene oxide or copolymerization of two or more alkylene oxides, thus giving a polymer with a high degree of polymerization. However, it is pointed out that the above conventional processes have problems in that the reproducibility, for example, of the polymerization rate and the degree of polymerization of the resultant polymer, is bad, and the sufficient yield cannot be obtained, or the polymerization product is lumped, so the polymer cannot industrially stably be produced. Furthermore, the degree of polymerization is still not sufficiently satisfactory.

On the other hand, a process is attempted to obtain a polymer with good reproducibility by using a catalyst comprising a product from a reaction between an organozinc compound and a polyhydric alcohol, which reaction is carried out under conditions where various fine particle metal oxides (dispersion promoters) and nonionic surfactants are in contact with each other in an inactive medium (EP 239,973 and U.S. Pat. No. 4,667,013). However, it is pointed out that this process has disadvantages in that the operation of preparing the catalyst is very complicated. Specifically, because no reversed micelle is formed in spite of the use of the surfactant, a long-time stirring is needed for dispersing a polyhydric alcohol such as 1,4-butanediol into a hexane solvent wherein the polyhydric alcohol is insoluble in the hexane solvent, and further, the stirring conditions need high technique and/or skill in order to disperse 1,4-butanediol in the form of finer liquid drops. Therefore, only particular technicians can perform the preparation of high active catalysts.

In addition, EP 239,973 and U.S. Pat. No. 4,667,013 above have no disclosure about a catalyst for polymerization of an alkylene oxide, which catalyst is prepared in a reaction field that is a reversed micelle of a W/O system in which the polyhydric alcohol such as 1,4-butanediol is the "water system," and a hydrocarbon solvent is the "oil system."

DISCLOSURE OF THE INVENTION

Objects of the Invention

An object of the present invention is to provide a production process for a polyalkylene oxide with fast polymerization reaction rate and good production efficiency.

Another object of the present invention is to provide a catalyst for polymerization and a dispersion thereof, which catalyst is effective for the above production process for a polymer such as polyalkylene oxide.

Yet another object of the present invention is to provide an organometallic fine particle and a production process therefor, which particle is, for example, useful as the above catalyst for polymerization.

SUMMARY OF THE INVENTION

The present inventors diligently studied about a process for stably producing an alkylene oxide polymer of high polymerization degree from an organometallic compound and either one or both of a polyhydric alcohol and a monohydric alcohol in a short polymerization time with good reproducibility in view of the above-mentioned situation. As a result, the inventors completed the present invention by finding that:

the polyhydric alcohol is formed into a micelle with a surfactant, whereby the polyhydric alcohol is allowed to fall into a solubilized and hyperfinely dispersed state in an inactive medium;

the organometallic compound is reacted upon the monohydric alcohol in the resultant micelle system including the hyperfinely dispersed polyhydric alcohol as the reaction field, thus preparing a polymerization catalyst for polyalkylene oxide; and if the polymerization of the alkylene oxide is performed using the polymerization catalyst as prepared in the above micelle system as the reaction field, then the alkylene oxide polymer can be synthesized with very good reproducibility and further in a short time with a extremely small amount of the catalyst.

In addition, unlike the process as disclosed in EP 239,973 and U.S. Pat. No. 4,667,013 above, the above micelle formation needs no skill of stirring. It is possible to easily form the micelle with an extremely conventional stirrer in a relatively short time including a stirring time of several minutes to about 1 hour. In addition, if the micelle is once formed, no component corresponding to the polyhydric alcohol (as the reaction field) precipitates even though the stirring is stopped. Thus, it is very simple. Furthermore, the solubilization by forming the micelle makes it unnecessary to use the dispersion promotor (as disclosed in EP 239,973 and U.S. Pat. No. 4,667,013 above) as an essential component.

Thus, a production process for an organometallic fine particle, according to the present invention, comprises the step of reacting an organometallic compound and a compound (I) in a micelle as a reaction field, wherein the compound (I) is at least one member selected from the group consisting of water and active-hydrogen-containing compounds which have one or more carbon atoms, and wherein the organometallic compound is shown by the following general formula (1):

$$R_xM \qquad (1)$$

wherein: R is a hydrocarbon group having one or more carbon atoms;
M is a metal that shows Pauling's electronegativity of 0.5–3.0;
x is the valence of M.

An organometallic fine particle, according to the present invention, comprises a structural unit of the general formula (2) below:

$$(-M-O-Y-O-) \qquad (2)$$

wherein: Y is a hydrocarbon group having one or more carbon atoms;
M is a metal that shows Pauling's electronegativity of 0.5–3.0;
and this particle has a total content of silica, magnesia, and alumina of 2 weight % or less and displays a sedimentation velocity of 1 hour or more.

DETAILED DESCRIPTION OF THE INVENTION

<About Organometallic Fine Particle>

The micelle, formed as the reaction field in the present invention, may be either an O/W type micelle or a W/O type micelle that is referred to as "reversed micelle." Which type of micelle is formed depends upon chemical species as used as the reaction field, and is therefore not especially limited. In addition, the chemical species, as used as the reaction field, is not especially limited, either. The organometallic compound might be used as the reaction field, or the compound (I) might be used as the reaction field. When a polyol and a monohydric alcohol are used as the compound (I), the polyol might be used as the reaction field, or the monohydric alcohol might be used as the reaction field.

The organometallic compound in the present invention is shown by the following general formula (1):

$$R_xM \qquad (1)$$

wherein: R is a hydrocarbon group having one or more carbon atoms;
M is a metal that shows Pauling's electronegativity of 0.5–3.0;
x is the valence of M.

The metal M is not especially limited if it shows Pauling's electronegativity of 0.5–3.0. Specific examples thereof include Li, Be, Na, Mg, K, Ca, Sc, Ti, V, Cr, Mn, Fe, Co, Ni, Cu, Zn, Al, Si, Ga, Ge, As, Se, Rb, Sr, Y, Zr, Nb, Mo, Tc, Ru, Rh, Pd, Ag, Cd, In, Sn, Sb, Te, Cs, Ba, Hf, Ta, W, Re, Os, Ir, Pt, Au, Hg, Ti, Pb, Bi, Po, Fr, Ra, La, Ce, Pr, Nd, Pm, Sm, Eu, Gd, Th, Dy, Ho, Er, Tm, Yb, Lu, Ac, Th, Pa, U, Np, Pu, Am, Cm, Bk, Cf, Es, Fm, Md, No, Lr. These metals may be used alone respectively, or in combinations with each other if necessary. Particularly preferable is at least one member selected from the group consisting of Be, Mg, Ca, Sr, Ba, Ra, Zn, and Al, because they give an organometallic fine particle with higher catalytic activity than other metals do.

Specific examples of the organometallic compound in the present invention include dimethylzinc, diethylzinc, dipropylzinc, diisopropylzinc, dibutylzinc, diisobutylzinc, di-t-butylzinc, dipentylzinc, dihexylzinc, diheptylzinc, dioctylzinc, di-2-ethylhexylzinc, diphenylzinc, ditolylzinc, dicyclobutylzinc, dicyclopentylzinc, di(methylcyclopentyl) zinc, dicyclohexylzinc, methylphenylzinc, ethylphenylzinc, calcium amide, calcium amide denatured products, trimethylaluminum, triethylaluminum, triisobutylaluminum, triisohexylaluminum, triphenylaluminum, diisobutylaluminum hydride, diethylaluminum chloride, diisobutylaluminum isopropoxide, aluminum methoxide, aluminum ethoxide, aluminum n-propoxide, aluminum isopropoxide, aluminum n-butoxide, aluminum isobutoxide, aluminum n-pentoxide, aluminum isopentoxide, aluminum 2-butoxide, aluminum t-butoxide, aluminum t-pentoxide, aluminum hydroxide, zinc dimethoxide, zinc diethoxide, zinc diisopropoxide, zinc di-n-propoxide, zinc di-n-butoxide, zinc diisobutoxide, zinc di-n-pentoxide, zinc diisopentoxide, zinc di-2-butoxide, zinc di-t-butoxide, zinc di-t-pentoxide, zinc hydroxide, calcium hydride, diethylcalcium, calcium dimethoxide, calcium diethoxide, calcium diisopropoxide, calcium di-n-propoxide, calcium di-n-butoxide, calcium diisobutoxide, calcium di-n-pentoxide, calcium diisopentoxide, calcium di-2-butoxide, calcium di-t-butoxide, calcium di-t-pentoxide, calcium hydroxide, dimethylmagnesium, diethylmagnesium, magnesium dimethoxide, magnesium diethoxide, magnesium diisopropoxide, magnesium di-n-propoxide, magnesium di-n-butoxide, magnesium diisobutoxide, magnesium di-n-pentoxide, magnesium diisopentoxide, magnesium, di-2-butoxide, magnesium di-tbutoxide, magnesium di-t-pentoxide, magnesium hydroxide, n-butylethylmagnesium. These organometallic compounds may be used alone respectively, or in combinations with each other if necessary. Particularly preferable is at least one member selected from the group consisting of alkylzincs (e.g. dimethylzinc, diethylzinc, dipropylzinc, diisopropylzinc, dibutylzinc, diisobutylzinc), alkylaluminums (e.g. trimethylaluminum, triethylaluminum, triisobutylaluminum), alkylmagnesiums (e.g. dimethylmagnesium, diethylmagnesium, n-butylethylmagnesium), and alkylcalciums (e.g. diethylcalcium), because these have good reactivity upon the compound (I), particularly, polyol and/or monohydric alcohol, and therefore facilitate the preparation of the fine particle, and further because they give an organometallic fine particle with higher catalytic activity than other organometallic compounds do. Especially when the organometallic fine particle of the present invention is used as the catalyst for polymerization of the alkylene oxide, the use of the dialkylzinc is preferable. In the case where organometallic compounds other than the dialkylzinc, such as dialkylmagnesium, is used, they merely have low reactivity upon the polyol, and it is therefore difficult to prepare a catalyst for polymerization having sufficient polymerization activity. In addition, in the case where the alkylaluminum is used, a catalyst for polymerization having polymerization activity to some degree may be obtained, but this catalyst tends to merely give a low-molecular polymer, and therefore cannot give a high-molecular and useful polyalkylene oxide.

In the present invention, the compound (I) is at least one compound selected from the group consisting of water and active-hydrogen-containing compounds which have one or more carbon atoms. The active-hydrogen-containing compound, having one or more carbon atoms, is not especially limited if it is a compound having one or more carbon atoms and an active-hydrogen-containing substituent such as a hydroxyl group, thiol group, amine group, carboxyl group, or sulfonic acid group. However, water and polyols are particularly preferable, because they give a more active catalyst than other compounds (I) do. In addition, it is particularly preferable to use a monohydric alcohol jointly with the water and the polyol as the compound (I).

Concrete examples of the polyol include ethylene glycol, diethylene glycol, triethylene glycol, tetraethylene glycol, 1,3-propanediol, 2-hydroxyethoxyisopropanol, 1,4-butanediol, 1,5-pentanediol, 1,6-hexanediol, cyclopentanediol, methylcyclopentanediol, cyclohexanediol, glycerin, resorcinol, catechol, hydroquinone. These polyols may be used alone respectively, or in combinations with each other if necessary. In addition, thioalcohol equivalents of these polyols can also be included in the above examples. When the organometallic fine particle of the present invention is used as the catalyst for polymerization of the alkylene oxide, it is preferable to use an aliphatic polyol having 2 to 6 carbon atoms. In the case where an aliphatic polyol having carbon atoms in number outside this range is used to prepare a catalyst for polymerization of the alkylene oxide, there are disadvantages in that the resultant catalyst merely has insufficient activity to polymerize the alkylene oxide. Particularly preferable is at least one member selected from the group consisting of water, ethylene glycol, diethylene glycol, triethylene glycol, butanediol, propanediol, and pentanediol.

Examples of the monohydric alcohol include methanol, ethanol, 1-propanol, 2-propanol, 1-butanol, 2-butanol, t-butanol, phenol, amyl alcohol, hexanol, heptanol, octanol, ethylhexanol, nonanol, decanol, undecanol, dodecanol, trimethylnonyl alcohol, tetradecanol, heptadecanol, cyclohexanol, 2-methylcyclohexanol, benzyl alcohol, glycidol, furfuryl alcohol, tetrahydrofurfuryl alcohol, α-terpineol alcohol, abiethyl alcohol, trichloroethanol, trifluoroethanol. These monohydric alcohols may be used alone respectively, or in combinations with each other if necessary. In addition, thioalcohol equivalents of these monohydric alcohols can also be included in the above examples. When the organometallic fine particle of the present invention is used as the catalyst for polymerization of the alkylene oxide, it is preferable to use a monohydric alcohol having 1 to 10 carbon atoms. In the case where the number of the carbon atoms is larger than this range, there are disadvantages in that: the substituent is too bulky to sufficiently react upon materials for preparation such as diethylzinc, so the preparation of the aimed catalyst for polymerization cannot adequately be carried out, and the resultant catalyst, therefore, merely has insufficient activity to polymerize the alkylene oxide. Particularly preferable is at least one member selected from the group consisting of methanol, ethanol, 1-propanol, 2-propanol, 1-butanol, 2-butanol, t-butanol, amyl alcohol, and hexanol. The use of the monohydric alcohol gives a fine particle with higher catalytic activity, but even if no monohydric alcohol is used, the high catalytic activity might be obtained, so the use of the monohydric alcohol is not essential.

In the present invention, it is preferable that the micelle is formed in an inactive medium. The inactive medium is a substance that is inactive upon the compound (I), in which the compound (I) is formed into a micelle with a solubilizing agent and is thereby dissolved.

In the present invention, a solvent having a solubility parameter of 40–25.0 [δ value: $(cal \cdot cm^{-3})^{1/2}$] is preferably used as the inactive medium. Specific examples of the inactive medium include n-pentane, n-hexane, isohexane, n-heptane, n-octane, isooctane, n-decane, 2,2-dimethylbutane, petroleum ether, petroleum benzine, ligroin, gasoline, kerosene, petroleum spirit, petroleum naphtha, 2-pentene, mixed pentane, cyclohexane, methylcyclohexane, methylcyclopentane, benzene, toluene, xylene, ethylbenzene, diethylbenzene, isopropylbenzene, amylbenzene, diamylbenzene, triamylbenzene, tetraamylbenzene, dodecylbenzene, didodecylbenzene, amyltoluene, coal tar naphtha, solvent naphtha, p-cymene, naphthalene, tetralin, decalin, biphenyl, dipentene, turpentine oil, pinene, p-menthane, pine oil, camphor oil, methyl chloride, methylene chloride, chloroform, carbon tetrachloride, ethyl chloride, ethylene chloride, ethylidene chloride, 1,1,1-trichloroethane, 1,1,2-trichloroethane, 1,1,1,2-tetrachloroethane, 1,1,2,2-tetrachloroethane, pentachloroethane, hexachloroethane, vinylidene chloride, 1,2-dichloropropane, butyl chloride, amyl chloride, mixed amyl chloride, dichloropentane, hexyl chloride, 2-ethylhexyl chloride, methyl bromide, ethyl bromide, ethylene bromide, tetrabromoethanechlorobromomethane, ethylene chlorobromide, chlorobenzene, o-dichlorobenzene, 1,2,4-trichlorobenzene, bromobenzene, o-dibromobenzene, o-chlorotoluene, p-chlorotoluene, α-chloronaphthalene, naphthalene chloride, fluorodichloromethane, dichlorodifluoromethane, fluorotrichloromethane, trifluoromonobromomethane, difluorochloroethane, 1,1,2-trichloro-1,2,2-trifluoroethane, ethyl ether, dichloroethyl ether, isopropyl ether, n-butyl ether, diisoamyl ether, n-hexyl ether, methyl phenyl ether, ethyl phenyl ether, n-butyl phenyl ether, amyl phenyl ether, o,m,p-cresyl methyl ether, p-t-amylphenyl n-amyl ether, ethyl benzyl ether, 1,4-dioxane, trioxane, furan, furfural, dioxolane, 2-methylfuran, tetrahydrofuran, cineol, methylal, diethylacetal, acetone methylacetone, methyl ethyl ketone, methyl n-propyl ketone, methyl n-butyl ketone, rnethyl isobutyl ketone, methyl n-amyl ketone, methyl n-hexyl ketone, diethyl ketone, ethyl n-butyl ketone, di-n-propyl ketone, diisobutyl ketone, 2,6,8-trimethylnonanone-4, acetone oil, acetonylacetone, mesityl oxide, phorone, isophorone, cyclohexanone, methylcyclohexanone, acetophenone, dypnone, camphor, methyl formate, ethyl formate, propyl formate, n-butyl formate, isobutyl formate, methyl acetate, ethyl acetate, n-propyl acetate, isopropyl acetate, n-butyl acetate, isobutyl acetate, secondary-butyl acetate, n-amine acetate, isoamyl acetate, methylisoamyl acetate, methoxybutyl acetate, secondary-hexyl acetate, 2-ethylbutyl acetate, methylisobutylcarbinol acetate, 2-ethylhexyl acetate, cyclohexyl acetate, methylcyclohexyl acetate, benzyl acetate, methyl propionate, ethyl propionate, n-butyl propionate, isoamyl propionate, methyl butyrate, ethyl butyrate, n-butyl butyrate, isoamyl butyrate, ethyl oxyisobutyrate, butyl stearate. amyl stearate. methyl acetoacetate, ethyl acetoacetate, isoamyl isovalerate, methyl lactate, ethyl lactate, butyl lactate, amyl lactate, methyl benzoate, ethyl benzoate, propyl benzoate, butyl benzoate, isoamyl benzoate, benzyl benzoate, ethyl cinnamate, methyl salicylate, octyl adipate, diethyl oxalate, dibutyl oxalate, diamyl oxalate, diethyl malonate, dibutyl tartrate, tributyl citrate, dioctyl sebacate, dimethyl phthalate, diethyl phthalate, dibutyl phthalate, di-2-ethylhexyl phthalate, dioctyl phthalate, nitromethane, nitroethane, nitropropane, nitrobenzene, nitroanisole, monomethylamine, dirnethylamine, trimethylamine, monoethylamine, diethylamine, triethylamine, aniline, toluidine, acetoamide, acetonitrile, benzonitrile, pyridine, picoline, lutidine, quinoline, morpholine, carbon disulfide, dimethyl sulfoxide, propanesulfone, triethyl phosphate. These inactive media may be used alone respectively, or in combinations with each other if necessary. Particularly preferable is at least one member selected from the group consisting of cyclohexane, isooctane, n-heptane, n-dodecane, chloroform, and benzene, because they give an organometallic fine particle with higher catalytic activity than other inactive media do.

In the present invention, the compound (I) is formed into a micelle with a solubilizing agent and is thereby dissolved into the inactive medium. An amphiphilic solvent or a surfactant is preferably used as such a solubilizing agent. The surfactant may be any one of cationic, anionic, amphoteric, and nonionic surfactants, but ionic surfactants are preferable, and particularly, the anionic surfactant is preferable, because the anionic surfactant is suitable for forming a micelle or a reversed-micelle from the inactive medium and the polyol.

Specific examples of the amphiphilic solvent include acetonitrile, 1,4-dioxane, trioxane, tetrahydrofuran, acetone, methylacetone, methyl ethyl ketone, methyl n-propyl ketone, dioxolane.

In addition, examples of the surfactant include: anionic surfactants, such as fatty acid soaps (e.g. sodium salts and/or potassium salts of aliphatic carboxylic acids such as lauric acid, myristic acid, palmitic acid, stearic acid, and oleic acid), N-acyl-N-methylglycine salts, N-acyl-N-methyl-β-alanine salts, N-acylglutamic acid salts, polyoxyethylene alkyl ether carboxylic acid salts, acylated peptide, alkylbenzenesulfonic acid salts, alkylnaphthalenesulfonic acid salts, naphthalenesulfonic acid salt-formalin polycondensation products, melaminesulfonic acid salt-formalin polycondensation products, dialkylsulfosuccinic acid ester salts, alkyl sulfosuccinate disalts, polyoxyethylene alkylsulfosuccinic acid disalts, alkylsulfoacetic acid salts, α-olefinsulfonic acid salts, N-acylmethyltaurine salts, sodium dimethyl 5-sulfoisophthalate, sulfonated oil, higher alcohol sulfuric acid ester salts, polyoxyethylene alkyl ether sulfuric acid salts, secondary higher alcohol ethoxysulfate, polyoxyethylene alkyl phenyl ether sulfuric acid salts, monoglysulfate, sulfuric acid ester salts of fatty acid alkylolamides, polyoxyethylene alkyl ether phosphoric acid salts, polyoxyethylene alkyl phenyl ether phosphoric acid salts, alkylphosphoric acid salts, sodium bistridecylsulfosuccinate, sodium dioctylsulfosuccinate, sodium dihexylsulfosuccinate, sodium dicyclohexylsulfosuccinate, sodium diamylsulfosuccinate, sodium diisobutylsulfosuccinate, disodium sulfosuccinate ethoxylated alcohol half esters, disodium sulfosuccinate ethoxylated nonylphenol half esters, disodium isodecylsulfosuccinate, disodium N-octadecylsulfosuccinamide, tetrasodium N-(1,2-dicarboxyethyl)-N-octadecylsulfosuccinamide, ammonium nonylphenoxypoly(ethylenoxy)ethanolsulfate, disodium mono- and didodecyldiphenyl oxide disulfonates, sodium diisopropylnaphthalenesulfonate, and neutralized condensation products from sodium naphthalenesulfonate; cationic surfactants, such as aliphatic amine salts, aliphatic quaternary ammonium salts, benzalkonium salts, benzethonium chloride, pyridi-nium salts, imidazolium salts, and alkylamineguanidinepolyoxyethanol; amphoteric ionic surfactants, such as carboxybetaine types, aminocarboxylic acid salts, imidazolinium betaine, lecithin, and alkylamine oxide; nonionic surfactants, such as adducts of n mols of ethylene oxide to nonylphenol (n is 1 or more), adducts of n mols of ethylene oxide to lauryl alcohol (n is 1 or more), adducts of n mols of ethylene oxide to alkylphenols (n is 1 or more), adducts of n mols of ethylene oxide to fatty acids (n is 1 or more), adducts of n mols of ethylene oxide to stearic acid (n is 1 or more), polyoxyethylene alkyl ethers, polyoxyethylene alkyl phenyl ethers, alkylallylformaldehyde-condensed polyoxyethylene ethers, polyoxyethylene polyoxypropyl alkyl ethers, polyoxyethylene ethers of glycerol esters, polyoxyethylene ethers of sorbitan esters, polyoxyethylene ethers of sorbitol esters, polyethylene glycol fatty acid esters, glycerol esters, polyglycerol esters, sorbitan esters, propylene glycol esters, sucrose esters, fatty acid alkanolamides, polyoxyethylene fatty acid amides, polyoxyethylene alkylamines, amine oxides, single chain length polyoxyethylene alkyl ethers, polyoxyethylene secondary-alcohol ethers, polyoxyethylene sterol ethers, polyoxyethylene lanolin derivatives, ethylene oxide derivatives of alkylphenol-formalin-condensed products, polyoxyethylene-polyoxypropylene block copolymers, polyoxyethylene propyl alkyl ethers, polyoxyethylene glycerol fatty acid esters, (cured) polyoxyethylene castor oils, polyoxyethylene sorbitan fatty acid esters, polyoxyethylene sorbitol fatty acid esters, polyoxyethylene fatty acid alkanolamide sulfuric acid salts, polyethylene glycol fatty acid esters, ethylene glycol fatty acid esters, fatty acid monoglyceride, polyglycerol fatty acid esters, sorbitan fatty acid esters, propylene glycol fatty acid esters, sucrose fatty acid esters, fatty acid alkanolamides, polyoxyethylene fatty acid amides, and polyoxyethylene alkylamines; and further, disodium N-perfluorooctanesulfonylglutamate, sodium 3-[fluoroalkyloxy]-1-alkylsulfonate, sodium 3-[ω-fluoroalkanoyl-N-ethylamino]-1-propanesulfonate, N-[3-(perfluorooctanesulfonamide)propyl]-N,N-dimethyl-N-carboxymethylene ammonium betaine, fluoroalkylcarboxylic acids, perfluoroalkylcarboxylic acids, perfluorooctanesulfonic acid diethanolamide, perfluoroalkylsufonic acid salts, N-propyl-N-(2-hydroxyethyl) perfluorooctanesulfonamide, propyltrimethylammonium perfluoroalkylsulfonamide, perfluoroalkyl-N-ethylsulfonylglycine salts, bis (N-perfluorooctylsulfony1-N-ethylaminoethyl)monoperfluoroalkylethyl phosphates, sulfuric acid ester salts of polyoxyethylene allylglycidylnonyl phenyl ethers, polyoxyethylene allylglycidylnonyl phenyl ethers, polyoxyethylene nonylpropenyl phenyl ethers, ammonium salts of polyoxyethylene nonylpropenyl phenyl ether sulfuric acid esters, high-molecular flocculants, flotation agents.

In addition, compounds having a reactive substituent such as hydroxyl, for example, the above specific examples of the nonionic surfactant other than polyoxyethylene alkylamines, are preferably converted into structures of such as methoxides with reactive treating agents and then used. Examples of the reactive treating agent include compounds with a substituent, such as isocyanates and ketenes, but the reactive treating agent is not especially limited if it eliminates the reactive substituent from the surfactant.

The above surfactants may be used alone respectively, or in combinations with each other if necessary.

The amount of the solubilizing agent, as added in the present invention, optionally changes dependently upon chemical species as the reaction field, and is therefore not especially limited. For example, the amount of the ionic surfactant, as added, is preferably at least 0.1 weight %, more preferably at least 5 weight %, still more preferably at least 20 weight %, of the polyol and/or the monohydric alcohol. In the case where the amount of the ionic surfactant, as added, is smaller than the above ranges, there are disadvantages in that no effect of the addition of the surfactant can be exhibited or no high active catalyst can be prepared, because the polyol and/or the monohydric alcohol cannot fully form a micelle in the inactive medium. Or otherwise in the case where the amount of the ionic surfactant, as added, is extremely large, a large amount of surfactant vainly does not take part in the formation of the micelle. Such a surfactant remains in the inactive medium and therefore can be recovered along with the inactive medium and then used for the next catalyst preparation.

The water content of the surfactant in the present invention is not especially limited, but it is preferably as low as possible. In the case where the water content of the surfactant is high, there are disadvantages in that: water changes the charging ratio of the organometallic compound to the polyhydric or monohydric alcohol, or destroys the organometallic compound to convert it into such as a hydroxide, and thus the aimed catalyst structure is not obtained or the purity of the resultant catalyst is low, so the catalytic activity is not displayed or is low. The water content of the surfactant is preferably 5 weight % or lower, more preferably 1 weight % or lower, still more preferably 0.5 weight % or lower, most preferably 0.05 weight % or lower.

The preparation of the organometallic fine particle in the present invention is usually performed under an atmosphere of an inert gas such as nitrogen, argon, helium, neon, or carbonic acid gas. The amount of active protons in the reaction system in the preparation of the fine particle is preferably 500 ppm or less. The amount of active protons in the reaction system denotes: moisture as attached to such as reaction vessels; water as contained in the starting materials such as inactive medium, polyol, monohydric alcohol, inert gas, and organometallic compound; and materials unnecessary for the preparation of the fine particle, such as alcoholic compounds or acid compounds (e.g. carboxylic compounds). The amount of active protons in the reaction system is more preferably 200 ppm or less, still more preferably 100 ppm or less, and most preferably 50 ppm or less. In the case where the amount of active protons in the reaction system is larger than the above-mentioned ranges, there are disadvantages in that a reaction between the organometallic compound and the active proton occurs to disable the preparation of a catalyst having activity as needed for polymerization, or in that even if a catalyst having polymerization activity could be prepared, its activity would not be very high.

The preparation process for the fine particle in the present invention is, for example, preferably carried out in the inactive medium as follows: the organometallic compound is reacted upon the polyol in a first step, and then further reacted upon the monohydric alcohol in a second step, thus obtaining the catalyst. Or otherwise, it is also permitted that the organometallic compound is reacted upon the monohydric alcohol in the first step, and then upon the polyol in the second step.

The ratio by equivalent of the polyol to the organometallic compound is in the range of usually 0.1 to 1.8, preferably 0.3 to 1.1, more preferably 0.4 to 0.9. In the case where the quantity of the polyol is outside the above-mentioned ranges, the polymerization rate will fall extremely.

The ratio by equivalent of the monohydric alcohol to the organometallic compound is in the range of usually 0.0 to 1.0, preferably 0.1 or more, but even if this ratio is 0.0, an active catalyst is obtainable. In addition, in the case where the quantity of the monohydric alcohol is larger than the above-mentioned range, it is enough to remove an excess of the monohydric alcohol by means such as devolatilization under reduced pressure after the preparation of the fine particle has been completed.

The temperature, at which the preparation of the fine particle is carried out, is in the range of preferably −50~300° C., more preferably 0~200° C., still more preferably 20~150° C. In the case where the fine particle preparation temperature is lower than the above-mentioned ranges, there are disadvantages in that the resultant polymerization activity is low, because the rate of the reaction between the organometallic compound and the compound (I) is so remarkably low that it takes a long time to prepare the fine particle or that the reaction does not fully run. On the other hand, in the case where the catalyst preparation temperature is higher than the above-mentioned ranges, there are disadvantages in that the resultant catalyst merely has so remarkably low polymerization activity that the polymerization needs a very long time.

After being prepared, the fine particle may be heated, but this heating treatment must not necessarily be carried out. This heating treatment is particularly effective for conventional catalyst preparation processes as carried out without using the micelle as the reaction field, but is not necessarily effective for the present invention because the micelle is used as the reaction field in the present invention. If the heating treatment of the fine particle is performed, the polymerization reaction of the alkylene oxide using the heated fine particle as the polymerization catalyst can give an alkylene oxide polymer with very good reproducibility and further in a short time with a extremely small amount of the catalyst. In addition, depending on conditions, this catalyst might give an alkylene oxide polymer that unexpectedly has a greatly high polymerization degree when compared with polymers as obtained conventionally. The heating treatment may be performed using a high boiling point hydrocarbon solvent, or at 100° C. or higher under high pressure with an autoclave. The temperature in the heating treatment is usually in the range of 20–200° C. The temperature lower than 20° C. provides almost the same result as of no heating treatment: for example, the reproducibility of such as polymerization rate and polymerization degree of the resultant polymer is bad. The temperature exceeding 200° C. has the disadvantage of giving such a remarkably low active catalyst that a very long time is needed for polymerization.

In addition, a dispersion promotor may be used to prepare the fine particle. Examples of the dispersion promotor include fumed silica, fumed magnesia, fumed alumina, fumed titania, fumed zirconia, calcium carbonate, titanium oxide, zirconium oxide, aluminum oxide, zinc oxide, magnesium oxide, silicon oxide, acid zinc, magnesium carbonate, diatomite, talc, mica, Aerosil (Degussa Corporation). These may be used alone respectively, or in combinations with each other if necessary.

The amount of the dispersion promotor, as added, is preferably 0.01 weight % or more of the inactive medium that is a solvent for preparation of the fine particle. Adding the dispersion promotor enlarges the bulk density of a polyalkylene oxide as obtained by polymerizing an alkylene oxide using the resultant fine particle as the catalyst for polymerization. Thus, the amount of the dispersion promotor, as added, is not limitative, and the amount smaller than the above range has the disadvantage of losing the effect of the addition.

However, in the present invention, unlike the foregoing EP 239,973 and U.S. Pat. No. 4,667,013, the addition of the dispersion promotor is not essential to the preparation of the catalyst. Even if no dispersion promotor is added, it is possible to synthesize a catalyst of very high activity for polymerization of the alkylene oxide.

In the present invention, there is no especial problem about the radius of the droplet as formed inside the reversed micelle and/or the micelle if it is 1.0 $\mu$m or less. This radius is preferably 0.5 $\mu$m or less, and more preferably 0.1 $\mu$m or less. In the case where the radius of the droplet as formed inside the reversed micelle and/or the micelle is larger than the above-mentioned ranges, there are disadvantages in that so excessively large a quantity of polyol component is present in the reaction field that the polyol component aggregates to merely give a catalyst of large particle diameter. Such a catalyst merely has low polymerization activity, so it is meaningless to prepare this catalyst using the solubilizing agent.

The organometallic fine particle, according to the present invention, comprises a structural unit of the general formula (2) below:

$$(M-O-Y-O-) \quad (2)$$

wherein: Y is a hydrocarbon group having one or more carbon atoms;

M is a metal that shows Pauling's electronegativity of 0.5–3.0; and this particle has a total content of silica, magnesia, and alumina of 2 weight % or less and displays a sedimentation velocity of 1 hour or more.

The hydrocarbon group Y in general formula (2) derives from the compound (I) that is used to produce the particle and has active hydrogen. This hydrocarbon group Y is not especially limited if it is a hydrocarbon group as shown by $C_nC_m$ ($n \geq 1$, $m \geq 2$). The hydrocarbon group Y may be an aliphatic one (including linear, cyclic, unsaturated, or saturated type), or an aromatic one, or a combined hydrocarbon group of both the aliphatic and aromatic ones. Examples thereof include 

The silica, magnesia, or alumina, as contained in the organometallic fine particle, is mainly the residue of those as used in the production step. As is aforementioned, in the present invention production process, the addition of the dispersion promotor (such as silica, magnesia, or alumina) is not essential, and it is therefore possible to produce the organometallic fine particle having the low total content of silica, magnesia, and alumina. Specifically, such a content is 2 weight % or less of the dried organometallic fine particle. Because the organometallic fine particle according to the present invention has the low total content of silica, magnesia, and alumina of 2 weight % or less, it is avoidable for the organometallic fine particle to aggregate due to non-uniform dispersing of the dispersion promotor into the inactive medium when the organometallic fine particle is prepared. In addition, there are advantages in that, because of little use of the water-insoluble dispersion promotor such as silica, magnesia, or alumina, the amount of water-insoluble component is small when a polymer, which is used in the dissolved state in water, such as polyalkylene oxide, is synthesized and used.

In addition, the present invention production process can give a particle having a fine particle diameter, because the micelle is used as the reaction field. The smaller the particle diameter is, the slower the sedimentation velocity is. As to the organometallic fine particle according to the present invention, the sedimentation velocity is at least 1 hour, preferably at least 3 hours, more preferably at least 5 hours, most preferably at least 10 hours. Incidentally, the sedimentation velocity is defined by the measurement method as described in the below-mentioned "BEST MODE FOR CARRYING OUT THE INVENTION" portion hereof.

The content of the ionic surfactant in the present invention organometallic fine particle is not especially limited, but is preferably at least 0.01 weight %, more preferably at least 0.1 weight %, still more preferably at least 1 weight %, most preferably at least 5 weight %. In the case where the content of the ionic surfactant in the present invention organometallic fine particle is smaller than these ranges, there are disadvantages in that the function to carry out the polymerization while preventing the electrification, which function is an feature of the present invention, is deteriorated. In the reaction to carry out the polymerization involving the friction between powders, like in the use of an organic solvent as the inactive medium or in the precipitation polymerization, unless the electrification due to static electricity is prevented, ignition to the organic solvent occurs, so there are very serious problems of the safety. In addition, the occurrence of the static electricity during the polymerization reaction unfavorably causes the aggregation of the resultant polymer.

<About polymerization>

The present invention organometallic fine particle is very useful as a catalyst for polymerization.

The monomer, which is polymerized using the present invention organometallic fine particle as the catalyst for polymerization, is not especially limited, but the present invention organometallic fine particle displays ionic polymerizability and is therefore appropriate for polymerization of ionic-polymerizable monomers.

The ionic-polymerizable monomer is not especially limited if it is a reactive monomer having anionic polymerizability, ring-opening polymerizability, coordinated anionic polymerizability or cationic polymerizability.

Examples of the anionic-polymerizable monomer include cyclic ether compounds, aldehyde compounds, olefin compounds, lactone compounds, lactam compounds, cyclic thioether compounds, carbonate compounds, acid anhydrides, amine compounds, hetero-multiple-bonded compounds.

Specific examples of the aldehyde compound include acetoaldehyde, methyl glyoxylate, ethyl glyoxylate, glyoxal, formaldehyde, propionaldehyde, butyraldehyde, isobutyraldehyde, valeraldehyde, isovaleraldehyde, pivalaldehyde, capronaldehyde, heptaldehyde, caprylaldehyde, pelargonaldehyde, caprinaldehyde, undecylaldehyde, laurylaldehyde, tridecylaldehyde, myristic aldehyde, pentadecylaldehyde, palmitic aldehyde, margaric aldehyde, stearic aldehyde, succindialdehyde, acrolein, crotonaldehyde, benzaldehyde, o-tolualdehyde, p-tolualdehyde, m-tolualdehyde, salicylaldehyde, cinnamaldehyde, a-naphthaldehyde, β-naphthaldehyde, furfural.

Specific examples of the hetero-multiple-bonded compound include carbon dioxide, sulfur dioxide, carbon monoxide, sulfur monoxide, nitrogen monoxide, nitrogen dioxide, carbon disulfide, carbonyl compounds, thiocarbonyl compounds, nitroso compounds, nitrile compounds, ketene compounds, isocyanic acid compounds, thioisocyanic acid compounds, isonitrile compounds, quinone compounds, imine compounds, disilene compounds.

Specific examples of the cyclic thioether compound include thioethylene oxide, thiopropylene oxide, thiocyclohexene oxide, thiostyrene oxide, thioepoxybutane, thioepoxybutene, thioepichlorohydrin, thioallyl glycidyl ether, thiophenyl glycidyl ether, thiotetrahydrofuran, thiooxetane, thiodioxolane, thiodioxane.

Specific examples of the olefin compound include: styrenes, such as styrene, p-methoxystyrene, and N,N'-dimethyl-p-styrenevinylnaphthalene; unsaturated hydrocarbons, such as acetylene, acetylene compounds, ethylene, propylene, butadiene, isoprene, and vinylphenol, vinyl ethers, such as methyl vinyl ether, ethyl vinyl ether, propyl vinyl ether, and butyl vinyl ether; acrylic acid; acrylic isters, such as methyl acrylate and ethyl acrylate, methacrylic acid; methacrylic esters such as methyl methacrylate and ethyl methacrylate.

Specific examples of the lactone compound include ε-caprolactone, propiolactone, butyrolactone, δ-valerolactone, coumarin, dimethylpropiolactone, caprylolactone, laurolactone, palmitolactone, stearolactone, crotolactone, α-angelicalactone, β-angelicalactone, lactide, glycolide.

Specific examples of the lactam compound include β-propiolactam, γ-butyrolactam, 2-piperidone, succinimide, δ-valerolactam, ε-caprolactam, heptolactam, lactimide, lactim.

Specific examples of the amine compound include ethylenimine, pyrrolidine, piperidine, piperadine.

Specific examples of the carbonate compound include ethylene carbonate, propylene carbonate.

Specific examples of the acid anhydride include succinic anhydride, maleic anhydride, itaconic anhydride, glutaric anhydride, adipic anhydride, citraconic anhydride, phthalic anhydride, trimellitic anhydride, butane-1,2,3,4-tetracarboxylic dianhydride, pyromellitic dianhydride, biphenyltetracarboxylic dianhydride, p-terphenyl-3,4,3',4'-tetracarboxylic dianhydride, 3,3',4,4'-benzophenonetetracarboxylic dianhydride, 1,2,3,4-cyclopentanetetracarboxylic dianhydride, naphthalene-1,4,5,8-tetracarboxylic dianhydride, 3,4,9,10-perylenetetracarboxylic dianhydride, 2,3,4,5-tetrahydrofurantetracarboxylic dianhydride, 3,3',4,4'-diphenylsulfonetetracarboxylic dianhydride, bicyclo[2.2.2]oct-7-ene-2,3,5,6-tetracarboxylic dianhydride.

Specific examples of the cyclic ether compound include ethylene oxide, propylene oxide, cyclohexene oxide, styrene oxide, butylene oxide, epoxybutane, epoxybutene, epichlorohydrin, allyl glycidyl ether, phenyl glycidyl ether, tetrahydrofuran, oxetane, dioxolane, dioxane.

As to the above ionic-polymerizable monomer, a homopolymer may be synthesized using one kind of ionic-polymerizable monomer, or a copolymer may be synthesized using two or more kinds of ionic-polymerizable monomers.

Considering the economical advantage and the reaction ease, cyclic ethers, particularly, ethylene oxide and propylene oxide, are preferable. In addition, ethylene oxide is more preferably excellent both in the economical advantage and the reactivity. If necessary, ethylene oxide may be partially or entirely replaced with another cyclic ether, preferably, in the ratio of 5–100%, more preferably 5–50%.

If desired, other starting materials which are ionic-polymerizable are also usable. The use of the present invention catalyst enables the production of an ionic-polymerized polymer with good efficiency.

The polymerization reaction, using the present invention organometallic fine particle as the catalyst for polymerization, can be performed by any method as desired. This method can be carried out in a batch manner, continuous manner, or semicontinuous manner, or in combination of these manners. The catalyst may be added all at once, or added intermittently little by little or continuously during the reaction. Similarly, the monomer can be continuously added into the reaction vessel. The polymerization can be performed without solvent, or in the inactive medium or in the presence of a diluent. The inactive medium or the diluent is not especially limited, and both are usable, if they are non-reactive upon the polymerization reaction or catalyst. Examples of the inactive medium or the diluent include hexane, cyclohecane, octane, isooctane, benzene, toluene, xylene, petroleum ether, chloroform, methylcyclopentane.

After the end of the polymerization reaction, any additive that is known to be usable and is innoxious can be added. These additives are well-known in the art, and examples thereof include antioxidants, heat stabilizers, photostabilizers, colorants, fillers, antistats.

Examples of the antioxidant, usable in the present invention, include phenolic antioxidants, sulfur-based antioxidants, phosphorus-based antioxidants, amine-based antioxidants.

Examples of the phenolic antioxidant include 2,4-bis-(n-octylthio)-6(4-hydroxy-3,5-t-butylanilino)-1,3,5-triazine, pentaerythrityl-tetrakis[3-(3,5-di-t-butyl-4-hydroxyphenyl) propionate] (trade name: IRGANOX 1010), 2,2-thiodiethylenebis[3-(3,5-di-t-butyl-4-hydroxyphenyl) propionate], 3,9-bis[2-(3-(3-t-butyl-4-hydroxy-5-methylphenyl)propionyloxy)-1,1-dimethylethyl]-2,4,8,10-tetraoxaspiro[5.5]undecane (trade name: Sumilizer GA-80), triethylene glycol bis[3-(3-t-butyl-5-methyl-4-hydroxyphenyl) propionate] (trade name: IRGANOX 45), 1,6-hexanediol bis[3-(3,5-di-t-butyl-5-methyl-4-hydroxyphenyl) propionate] (trade name: IRGANOX 259), tetrakis[methylene(3,5-di-t-butyl-4-hydroxyhydrocinnamate)]methane, octadecyl-3-(3,5-di-t-butyl-4-hydroxyphenyl) propionate] (trade name: IRGANOX 1076), diethyl 3,5-di-t-butyl-4-hydroxybenzylphosphonate (trade name: IRGANOX 1222), N,N'-hexamethylene-bis(3,5-di-t-butyl-4-hydroxyhydrocinnamamide), 1,3,5-trimethyl-2,4,6-tris(3,5-di-t-butyl-4-hydroxybenzyl)benzene, calcium bis(ethyl 3,5-di-t-butyl-4-hydroxybenzylphosphonate) (trade name: IRGANOX 1425 WL), tris(3,5-di-t-butyl-4-hydroxybenzyl) isocynurate (trade name: IRGANOX 3114), 1,1,3-tris(2-methyl-4-hydroxy-5-t-butylphenyl)butane, 2,2-bis[4-(2-(3,5-di-t-butyl-4-hydroxyhydrocinnamoyloxy))ethoxyphenyl] propane, 2,6-di-t-butyl-4 methylphenol.

Examples of the sulfur-based antioxidant include dilauryl 3,3-thiodipropionate(trade name: SUMILIZER TPL-R), dimyristyl 3,3-thiodipropionate (trade name: SUMILIZER TPM), distearyl 3,3-thiodipropionate (trade name: SUMILIZER TPS), pentaerythrityl (trade name: SUMILIZER TP-D), ditridecyl 3,3-thiodipropionate (trade name: SUMILIZER TL), 2-mercaptobenzimidazole (trade name: SUMILIZER MB).

Examples of the phosphorus-based antioxidant include the following compounds: hypophosphorous acid, phosphorous acid, and their esters, such as triphenyl phosphite, trilauryl phosphite, tris(nonylphenyl) phosphite, triisooctyl phosphite, triisodecyl phosphite, triphenyl phosphite, phenylisodecyl phosphite, diphenylisooctyl phosphite, diisooctylphenyl phosphite, tetrakis(2,4-di-t-butylphenyl)-4,4'-biphenylene phosphonite (trade name: IRGAFOS P-EPQF F), tris(2,4-di-t-butylphenyl) phosphite (trade name: IRGAFOS 168), distearylpentaerythritol diphosphite, dioctylpentaerythritol diphosphite, diisodecylpentaerythritol diphosphite, bis(2,4-di-t-butylphenyl)pentaerythritol diphosphite, bis(2,6-di-t-butyl-4-methylphenyl) pentaerythritol diphosphite (trade name: ADEKASTAB; tetrakis(2,4-di-t-butylphenyl)-4,4'-biphenylene phosphonite (trade name: SANDOSTAB P-EPQ); phosphoric acid and its esters, such as diphenyl phosphate, 2-ethylhexyldiphenyl phosphate, dibenzyl phosphate, triethyl phosphate, trimethyl phosphate, trioctyl phosphate, tricresyl phosphate, tris(4-t-butylphenyl) phosphate, tris(butoxyethyl) phosphate, and tri-n-butyl phosphate; hypophosphorous acid, polyphosphoric acid.

Examples of the amine-based antioxidant include phenyl-α-naphthylamine, phenyl-β-naphthylamine, N,N'-diphenyl-p-phenylenediamine, N,N'-di-β-phenylenediamine, N-cyclohexyl-N'-phenylene-p-phenylenediamine, N-phenylen e-N'-isopropyl-p-phenylenediamine, aldol-α-naphthylamine, 2,2,4-trimethyl-1,2-dihydroquinone polymer, 6-ethoxy-2,2,4-trimethyl-1,2-dihydroquinoline.

The above antioxidants may be used either alone respectively or in combinations with each other. For example, the phosphorus-based antioxidant, the sulfur-based antioxidant, and the amine-based antioxidant may jointly be used.

Examples of the antistat include the aforementioned anionic, cationic, amphoteric, and nonionic surfactants. The antistat may be either added after the formation of the polymer, or present in the reaction system during the polymerization reaction. Because the catalyst for polymerization comprising the organometallic fine particle, according to the present invention, involves the use of the above surfactant, this catalyst acts to prevent the electrification due to static electricity as caused during the polymerization reaction. Thus, if the polymerization of the alkylene oxide is carried out using the catalyst for polymerization comprising the organometallic fine particle according to the present invention, then the electrification can be prevented even without various additives to prevent the electrification, so that a polyalkylene oxide which aggregates little is obtainable.

In addition, additives, such as carbonic acid gas or fumed silica, may be used to prevent the aggregation during the polymerization.

During and/or after the polymerization, an agent having the ability to generate a radical may be added to adjust the molecular weight. Examples of this agent include 2,2'-azobis-(2,4-dimethylvaleronitrile), 2,2'azobis-(4-methoxy-2,4-dimethylvaleronitrile), hydrogen peroxide, ozone, perbenzoic acid, peracetic acid, m-chloroperbenzoic acid, 2,2'-azobisisobutyronitrile, 2,2'-azobis-(2-methylbutyronitrile), 1,1'-azobis-(cyclohexene-1-carbonitrile), 1-[1-cyano-1-methylethyl)azo]formamide, 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide], 2,2'-azobis(N-cyclohexyl-2-methylpropionamide], 2,2'-azobis[2-(5-methyl-2-imidazolin-2-yl)propane] dihydrochloride, 2,2'-azobis[2-(2-imidazolin-2-yl)propane] dihydrochloride, 2,2'-azobis[2-(2-imidazolin-2-yl)propane] disulfate dihydrate, 2,2'-azobis[2-(3,4,5,6-tetrahydropyridin-2-yl)propane] dihydrochloride, 2,2'-azobis{2-[1-(2-hydroxyethyl)-2-imidazolin-2-yl]propane} dihydrochloride, 2,2'-azobis[2-(2-imidazolin-2-yl)propane], 2,2'-azobis(2-methylpropionamidine) dihydrochloride, 2,2'-azobis[N-(2)-carboethyl)-2-methylpropionamidine], 2,2'-a zobis(2-methylpropionamideoxime), dimethyl-2,2'-azobisisobutyrate, 4,4'-azobis (4-cyanopentanoic acid), azodi-t-octane, isobutyl peroxide, α,α-bis(neodecan oylperoxy)diisopropylbenzene, cumyl peroxyneodecanoate, di-n-propyl peroxydicarbonate, diisopropyl peroxydicarbonate, 1,1,3,3-tetramethylbutyl peroxyneodecanoate, bis(4-t-butylcyclohexyl) peroxydicarbonate, 1-cyclohexyl-1-methylethyl peroxyneodecanoate, di-2-ethoxyethyl peroxydicarbonate, di-2-ethoxyhexyl peroxydicarbonate, t-hexyl peroxyneodecanoate, dimethoxybutyl peroxydicarbonate, di(3-methyl-3-methoxybutyl peroxy) dicarbonate, t-butyl peroxyneodecanoate, 2,4-dichlorobenzoyl peroxide, t-hexyl peroxypivalate, t-butyl peroxypivalate, 3,5,5-trimethylhexanoyl peroxide, octanoyl peroxide, lauryl peroxide, stearoyl peroxide, 1,1,3,3-tetramethylbutyl peroxy-2-ethylhexanoate, persuccinic acid. These may be added either alone or in combinations with each other.

The amount of the agent having the ability to generate a radical, as used, is optionally determined in accordance with the molecular weight of the undecomposed polyalkylene oxide, or in accordance with the desired molecular weight of the polyalkylene oxide as lowered by decomposition. If a large amount of the above agent is used for the undecomposed polyalkylene oxide, then a polyalkylene oxide with a lower molecular weight is obtainable.

The temperature, at which the agent having the ability to generate a radical is added, is not especially limited, but is preferably lower than the melting point of the resultant polyalkylene oxide for the purpose of obtaining the polyalkylene oxide in the form of remaining powdery. In addition, the above agent may be added either into the inactive medium, which is a solvent as used for the polymerization, or into the resultant polyalkylene oxide itself with no solvent. It is preferable that the above agent is added into the inactive medium (which is a solvent as used for the polymerization), because the molecular weight is more effectively reduced.

When the polymerization is carried out using the present invention organometallic fine particle as the catalyst for polymerization, chain transfer agents may be used to adjust the molecular weight. Examples of the chain transfer agent include: alcohols, such as methanol, ethanol, 1-propanol, 2-propanol, 1-butanol, 2-butanol, t-butanol, phenol, amyl alcohol, hexanol, heptanol, octanol, ethylhexanol, nonanol, decanol, undecanol, dodecanol, trimethylnonyl alcohol, tetradecanol, heptadecanol, cyclohexanol, 2-methylcyclohexanol, benzyl alcohol, glycidol, furfuryl alcohol, tetrahydrofurfuryl alcohol, α-terpineol alcohol, abiethyl alcohol, trichloroethanol, and trifluoroethanol; carboxyl-groupcontaining compounds, such as acetic acid and formic acid.

The polymerization temperature in the present invention is not especially limited. The polymerization can be carried out in the range of about −50 to about 150° C., and the polymerization temperature is preferably in the range of −10 to 65° C., more preferably 0 to 45° C. These temperatures are publicly known to be preferable in the art, and moreover, those operational temperatures are not critical in the present invention.

The polymerization pressure in the present invention is not especially limited, and the polymerization can be performed under atmospheric, reduced, or increased pressure. The pressure is preferably in the range of atmospheric pressure to 1.0 MPa. This range has advantages in that it is easy to perform the polymerization operation. However, it is possible to perform the polymerization even out of this range.

The polymerization operation is usually performed under an atmosphere of an inert gas such as nitrogen, argon, helium, neon, or carbonic acid gas. The amount of active protons in the reaction system in the polymerization operation is preferably 500 ppm or less. The amount of active protons in the reaction system denotes: moisture as attached to such as reaction vessels; water as contained in the starting materials such as inactive medium, monomer, and catalyst as prepared; and materials unnecessary for the polymerization reaction, such as alcoholic compounds or acid compounds (e.g. carboxylic compounds). The amount of active protons in the reaction system is more preferably 200 ppm or less, still more preferably 100 ppm or less, and most preferably 50 ppm or less. In the case where the amount of active protons in the reaction system is larger than the above-mentioned ranges, there are disadvantages in that a reaction between the organometallic compound and the active proton occurs to reduce the yield of a catalyst having activity as needed for polymerization, and to therefore deteriorate the polymerization activity or deactivate the catalyst itself.

The quantity of the catalyst, as used for the polymerization, is not especially limited, but the catalyst can be supplied in the range of 0.001 to 10.0 mol % in terms of metal atom M in proportion to the molar number of the monomer as supplied. Moreover, the resulting alkylene oxide polymer can easily be separated from the solvent in the form of fine particles without lumping.

When the organometallic fine particle of the present invention is used as the catalyst for polymerization, a powdery one easily hydrolyzes due to the moisture, as included in the air, to lose the catalytic activity, so it is preferable that the organometallic fine particle is used in the form of a dispersion (slurry) in which the organometallic fine particle is dispersed in an organic solvent.

The organic solvent to give the slurry of the organometallic fine particle is not especially limited if it is an inactive substance that does not react upon the organometallic fine particle. Specific examples of the organic solvent include n-pentane, n-hexane, isohexane, n-heptane, n-octane, isooctane, n-decane, 2,2-dimethylbutane, petroleum ether, petroleum benzine, ligroin, gasoline, kerosene, petroleum spirit, petroleum naphtha, 2-pentene, mixed pentane, cyclohexane, methylcyclohexane, methylcyclopentane, benzene, toluene, xylene, ethylbenzene, diethylbenzene, isopropylbenzene, amylbenzene, diamylbenzene, triamylbenzene, tetraamylbenzene, dodecylbenzene, didodecylbenzene, amyltoluene, coal tar naphtha, solvent naphtha, p-cymene, naphthalene, tetralin, decalin, biphenyl, dipentene, turpentine oil, pinene, p-menthane, pine oil, camphor oil, methyl chloride, methylene chloride, chloroform, carbon tetrachloride, ethyl chloride, ethylene chloride, ethylidene chloride, 1,1,1-trichloroethane, 1,1,2-trichloroethane, 1,1,1,2-tetrachloroethane, 1,1,2,2-tetrachloroethane, pentachloroethane, hexachloroethane, vinylidene chloride, 1,2-dichloropropane, butyl chloride, amyl chloride, mixed amyl chloride, dichloropentane, hexyl chloride, 2-ethylhexyl chloride, methyl bromide, ethyl bromide, ethylene bromide, tetrabromoethanechlorobromomethane, ethylene chlorobromide, chlorobenzene, o-dichlorobenzene, 1,2,4-trichlorobenzene, bromobenzene, o-dibromobenzene, o-chloro-toluene, p-chloro-toluene, α-chloronaphthalene, naphthalene chloride, fluorodichloromethane, dichlorodifluoromethane, fluorotrichloromethane, trifluoromonobromomethane, difluorochloroethane, 1,1,2-trichloro-1,2,2-trifluoroethane, ethyl ether, dichloroethyl ether, isopropyl ether, n-butyl ether, diisoamyl ether, n-hexyl ether, methyl phenyi ether, ethyl phenyl ether, n-butyl phenyl ether, amyl phenyl ether, o,m,p-cresyl methyl ether, p-t-amylphenyl n-amyl ether, ethyl benzyl ether, 1,4-dioxane, trioxane, furan, furfural, dioxolane, 2-methylfuran, tetrahydrofuran, cineol, methylal, diethylacetal, acetone methylacetone, methyl ethyl ketone, methyl n-propyl ketone, methyl n-butyl ketone, methyl isobutyl ketone, methyl n-amyl ketone, methyl n-hexyl ketone, diethyl ketone, ethyl n-butyl ketone, di-n-propyl ketone, diisobutyl ketone, 2,6,8-trimethylnonanone-4, acetone oil, acetonylacetone, mesityl oxide, phorone, isophorone, cyclohexanone, methylcyclohexanone, acetophenone, dypnone, camphor, methyl formate, ethyl formate, propyl formate, n-butyl formate, isobutyl formate, methyl acetate, ethyl acetate, n-propyl acetate, isopropyl acetate, n-butyl acetate, isobutyl acetate, secondary-butyl acetate, n-amine acetate, isoamyl acetate, methylisoamyl acetate, methoxybutyl acetate, secondary-hexyl acetate, 2-ethylbutyl acetate, methylisobutylcarbinol acetate, 2-ethylhexyl acetate, cyclohexyl acetate, methylcyclohexyl acetate, benzyl acetate, methyl propionate, ethyl propionate, n-butyl propionate, isoamyl propionate, methyl butyrate, ethyl butyrate, n-butyl butyrate, isoamyl butyrate, ethyl oxyisobutyrate, butyl stearate. amyl stearate. methyl acetoacetate, ethyl acetoacetate, isoamyl isovalerate, methyl lactate, ethyl lactate, butyl lactate, amyl lactate, methyl benzoate, ethyl benzoate, propyl benzoate, butyl benzoate, isoamyl benzoate, benzyl benzoate, ethyl cinnamate, methyl salicylate, octyl adipate, diethyl oxalate, dibutyl oxalate, diamyl oxalate, diethyl malonate, dibutyl tartrate, tributyl citrate, dioctyl sebacate, dimethyl phthalate, diethyl phthalate, dibutyl phthalate, di-2-ethylhexyl phthalate, dioctyl phthalate, nitromethane, nitroethane, nitropropane, nitrobenzene, nitroanisole, monomethylamine, dimethylamine, trimethylamine, monoethylamine, diethylamine, triethylamine, aniline, toluidine, acetoamide, acetonitrile, benzonitrile, pyridine, picoline, lutidine, quinoline, morpholine, carbon disulfide, dimethyl sulfoxide, propanesulfone, triethyl phosphate. These organic solvents may be used alone respectively, or in combinations with each other if necessary, and each of them can fitly be selected in accordance with the situation where the slurry containing the organometallic fine particle is used.

When the above slurry is used to synthesize the polyalkylene oxide, it is preferable that the organic solvent is n-pentane, n-hexane, isohexane, n-heptane, n-octane, isooctane, cyclohexane, or methylcyclopentane, because the use of these organic solvents makes it easy to dry the powder of the polyalkylene oxide, which is the resulting polymer, and because, as the polyalkylene oxide is insoluble in these organic solvents, the polyalkylene oxide can be handled in the form of remaining powdery without aggregating.

The organometallic fine particle of the present invention can be used not only as the polymerization catalyst, but also for other various purposes, for example: catalysts for transesterification; fillers, lubricants, reforming agents, and other additives, such as for rubber or plastic; and further, colorants and reforming agents, such as for printing ink, paints, or pigments.

BEST MODE FOR CARRYING OUT THE INVENTION

Hereinafter, the present invention is more specifically illustrated by the following examples of some preferred embodiments in comparison with comparative examples not according to the invention. However, the invention is not limited to the below-mentioned examples. Incidentally, the viscosity of the resultant alkylene oxide polymer and the sedimentation velocity of the resultant organometallic particle were determined by the methods as shown below.

The amount of the catalyst was described by weight in terms of zinc atom to facilitate the comparison.

MEASUREMENT OF THE MOLECULAR WEIGHT

The viscosity of 0.1 or 0.2 weight % aqueous solution, as obtained by dissolving the alkylene oxide polymer into ion-exchanged water, was measured with a B-type rotating viscometer to determine the molecular weight by a conventional method.

SEDIMENTATION VELOCITY

A slurry (volume of only powder=about 5 ml), in which the content of the organometallic fine particle resultant from each process is about 0.5 g (=¼ of the amount as prepared in each Example and Comparative Example) in terms of zinc atom, is transferred into a 100 ml measuring cylinder and then diluted to 100 ml with n-hexane. Thereafter, the diluted slurry is sufficiently stirred with a stirring rod such that the powder concentration will be uniform.

Thereafter, the stirring is stopped to settle the slurry, and a measurement is made about the time for the powder to sedimentate to or below 20 ml in calibrations of the measuring cylinder to such a degree that the supernatant becomes transparent. This time is taken as the sedimentation velocity.

In the above method, the finer the powder particles are, the longer the sedimentation time is; or otherwise, the more coarse the powder particles are, the shorter the sedimentation time is.

EXAMPLE 1

About 40 g of Aerosol OT-100 (chemical name: sodium dioctylsulfosuccinate: made by MITSUI CYTEC LTD.) was put into a 100 ml separable flask (to which agitation vanes for high viscosity were then fitted) and then devolatilized under high vacuum of about 130 Pa at 180° C. for about 5 hours to reduce the water content. Aerosol OT-100 was a transparent viscid liquid substance before the devolatilization, but changed into a light-yellow rigid fragile solid due to the devolatilization.

Next, 1.80 g of 1,4-butanediol, 24.0 g of Aerosol OT-100, as dehydrated by the above devolatilization, and 83.10 g of toluene were put into a 500 ml flask as thoroughly dried and thoroughly subjected to nitrogen substitution. Then, the contents of the flask were stirred at room temperature for about 30 minutes to form a reversed micelle from 1,4-butanediol with the Aerosol OT-100 to dissolve 1,4-butanediol into toluene, thus obtaining a colorless transparent liquid.

While the above-mentioned colorless solution was agitated at room temperature, 25 ml (about 18.37 g) of 20.7 weight % hexane solution of diethylzinc was dropped thereto over a period of about 1 hour with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.99 g of methanol and 12.53 g of toluene was dropped thereto over a period of about 40 minutes with a syringe. Thereafter, the resultant mixture was heated to about 40° C. and then agitated for 1 hour, thus obtaining a catalyst in the form of a hexane slurry containing a light-yellow, somewhat opaque, and fine powder. The sedimentation time of the resultant organometallic fine particle was 5 hours.

Next, 250 ml of dehydrated hexane and ⅒ (=0.201 g in terms of zinc atom) of the entirety of the catalyst slurry, as obtained by the abovementioned operation, were placed in sequence into a 1-liter autoclave and then put under a pressure of 0.4 MPa with a nitrogen gas. Then, 50.5 g of ethylene oxide was added to the autoclave to perform a polymerization reaction at 20° C. The polymerization finished in about 90 minutes after the initiation of the heat generation. As a result, a polyethylene oxide was obtained with a conversion of about 99%. The molecular weight thereof was about 4,000,000.

Comparative Example 1

First, 17 ml of dehydrated hexane and 25 ml (about 18.62 g) of 20.7 weight % hexane solution of diethylzinc were put into a 500 ml flask as thoroughly dried and thoroughly subjected to nitrogen substitution. Then, 1.79 g of 1,4-butanediol (in the form of a solution with a mixed solvent of 9.0 g of dehydrated tetrahydrofuran and 15 ml of dehydrated hexane) was dropped thereto at room temperature over a period of about 1 hour with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.99 g of methanol and 12.5 g of hexane was dropped thereto over a period of about 40 minutes with a syringe. Thereafter, the resultant mixture was heated to about 40° C. and then agitated for 1 hour, thus obtaining a catalyst in the form of a hexane slurry containing a white powder. The sedimentation time of the resultant organometallic fine particle was 50 minutes, when the sedimentation volume was already 10 ml or less.

Next, 250 ml of dehydrated hexane and ⅒ (=0.204 g in terms of zinc atom) of the entirety of the catalyst slurry, as obtained by the above-mentioned operation, were placed in sequence into a 1-liter autoclave and then put under a pressure of 0.34 MPa with a nitrogen gas. Then, 50.5 g of ethylene oxide was added to the autoclave to perform a polymerization reaction at 20° C. The polymerization finished in about 230 minutes after the initiation of the heat generation. As a result, a polyethylene oxide was obtained with a conversion of about 98%. The molecular weight thereof was about 4,500,000.

Comparative Example 2

First, 100 ml of dehydrated hexane, 3.09 g of (made by Degussa Corporation) Aerosil 380, and 3.60 g of 1,4-butanediol were put into a 500 ml flask as thoroughly dried and thoroughly subjected to nitrogen substitution. Then, the contents of the flask were stirred at room temperature for 2 hours. Next, 3.66 g of nonylphenol 10EO, which is a nonionic surfactant, was added thereto, and the resultant mixture was agitated at 45° C. for 1.5 hours. Next, 50 ml (36.83 g) of 20.7 weight % hexane solution of diethylzinc was dropped thereto over a period of about 15 minutes with a syringe. As a result, a gas was generated, and the heat generation was seen. In such a state, the agitation was continued for 2 hours. The contents of the flask were once cooled to room temperature, and then a solution of 2.86 g of ethanol in 23 g of dehydrated hexane was dropped thereto over a period of about 45 minutes. Finally, the contents of the flask were agitated at 45° C. for 1 hour.

As a result, the catalyst was obtained in the form of a slurry solution of a white powder. The sedimentation time of the resultant organometallic fine particle was 20 minutes, when the sedimentation volume was already 10 ml or less.

Next, 250 ml of dehydrated hexane and ⅟₂₀ (=0.201 g in terms of zinc atom) of the entirety of the catalyst slurry, as obtained by the above-mentioned operation, were placed in sequence into a 1-liter autoclave and then put under a pressure of 0.4 MPa with a nitrogen gas. Then, 50.5 g of ethylene oxide was added to the autoclave to perform a polymerization reaction at 20° C. The polymerization finished in about 180 minutes after the initiation of the heat generation. As a result, a polyethylene oxide was obtained with a conversion of about 98%. The molecular weight thereof was about 4,500,000.

As is evident from the results of Example 1 and Comparative Example 1 above, when the catalyst is prepared by forming a micelle using the anionic surfactant (Aerosol OT-100) as the solubilizing agent to carry out the polymerization, the polymerization time is shorter, in other words, the activity of the resultant catalyst is higher.

In addition, as is evident from the results of Example 1 and Comparative Example 2, the catalyst as obtained by forming a micelle using the anionic surfactant as the solubilizing agent shortens the polymerization time more greatly and therefore exhibits higher activity in the polymerization reaction when compared with the catalyst as obtained by the reaction in which the catalyst preparation was carried out using the nonionic surfactant and the silica dispersant.

In addition, the reason why the molecular weight of the polyalkylene oxide, as obtained using the high active catalyst, is low is because the use efficiency per catalyst is high and because the reaction rate is therefore accelerated. Moreover, as the use efficiency of the catalyst gets higher, it is possible to synthesize a better yield of polyalkylene oxide with a smaller amount of catalyst.

EXAMPLE 2

Aerosol OT-100 (chemical name: sodium dioctylsulfosuccinate: made by MITSUI CYTEC LTD.) was dehydrated by devolatilization under vacuum in the same way as of Example 1.

Next, 1.72 g of 1,4-butanediol, 24.98 g of Aerosol OT-100, as dehydrated by the above devolatilization, and 95.0 g of toluene were put into a 500 ml flask as thoroughly dried and thoroughly subjected to nitrogen substitution. Then, the contents of the flask were stirred at room temperature for about 30 minutes to form a reversed micelle from 1,4-butanediol with the Aerosol OT-100 to dissolve 1,4-butanediol into toluene, thus obtaining a colorless transparent liquid.

While the above-mentioned colorless solution was agitated at room temperature, 30 ml of hexane solution of diethylzinc of 1.0 mol/l was dropped thereto over a period of about 38 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.5 g of toluene is dropped thereto over a period of 12 minutes with a syringe. Thereafter, the resultant mixture was heated to about 40° C. and then agitated for 1 hour, thus obtaining a catalyst in the form of a hexane slurry containing a light-yellow, somewhat opaque, and fine powder.

Next, 250 ml of dehydrated hexane and $\frac{1}{20}$ (=0.0980 g in terms of zinc atom) of the entirety of the catalyst slurry, as obtained by the above-mentioned operation, were placed in sequence into a 1-liter autoclave and then put under a pressure of 0.34 MPa with a nitrogen gas. Then, 25 g of ethylene oxide was added to the autoclave to perform a polymerization reaction at 20° C. Twenty minutes later than the initiation of the reaction, 25 g of ethylene oxide was further added (so that the total of ethylene oxide as added would be 50 g). The reaction was stopped 40 minutes after the initiation of the reaction, and then ethylene oxide remaining unreacted was removed. The resultant polyethylene oxide was filtrated and then dried. The yield of the resultant polyethylene oxide was 44 g, and the conversion of the above reaction was 88%.

Comparative Example 3

First, 30 ml of dehydrated hexane and 30 ml of hexane solution of diethylzinc of 1.0 mol/l were put into a 500 ml flask as thoroughly dried and thoroughly subjected to nitrogen substitution. Then, 1.72 g of 1,4-butanediol (in the form of a solution with a mixed solvent of 11 g of dehydrated tetrahydrofuran and 5 g of dehydrated hexane) was dropped thereto at room temperature over a period of about 93 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.51 g of hexane was dropped thereto over a period of about 31 minutes with a syringe. Thereafter, the resultant mixture was heated to about 40° C. and then agitated for 1 hour, thus obtaining a catalyst in the form of a hexane slurry containing a white powder.

Next, 250 ml of dehydrated hexane and $\frac{1}{20}$ (=0.0980 g in terms of zinc atom) of the entirety of the catalyst slurry, as obtained by the above-mentioned operation, were placed in sequence into a 1-liter autoclave and then put under a pressure of 0.35 MPa with a nitrogen gas. Then, 25 g of ethylene oxide was added to the autoclave to perform a polymerization reaction at 20° C. Twenty minutes later than the initiation of the reaction, 25 g of ethylene oxide was further added (so that the total of ethylene oxide as added would be 50 g). The reaction was stopped 40 minutes after the initiation of the reaction, and then ethylene oxide remaining unreacted was removed. The resultant polyethylene oxide was filtrated and then dried. The yield of the resultant polyethylene oxide was 23 g, and the conversion of the above reaction was 46%.

As is evident from the results of Example 2 and Comparative Example 3 above, when the same amount of ethylene oxide is reacted for the very same time using the same amount of catalyst, the use of the catalyst as prepared with the reversed micelle of Example 2 gives about two times as much polyethylene oxide as Comparative Example 3.

Thus, it is clear that the productivity of the polyalkylene oxide per unit amount of catalyst per unit time is enhanced to about two times by using the catalyst as prepared with the reversed micelle.

EXAMPLE 3

Aerosol OT-100 (chemical name: sodium dioctylsulfosuccinate:
made by MITSUI CYTEC LTD.) was dehydrated by devolatilization under vacuum in the same way as of Example 1.

Next, 1.72 g of 1,4-butanediol, 24.98° of Aerosol OT-100, as dehydrated by the above devolatilization, and 95.0 g of toluene were put into a 500 ml flask as thoroughly dried and thoroughly subjected to nitrogen substitution. Then, the contents of the flask were stirred at room temperature for about 30 minutes to form a reversed micelle from 1,4-butanediol with the Aerosol OT-100 to dissolve 1,4-butanediol into toluene, thus obtaining a colorless transparent liquid.

While the above-mentioned colorless solution was agitated at room temperature, 30 ml of hexane solution of diethylzinc of 1.0 mol/l was dropped thereto over a period of about 38 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.5 g of toluene was dropped thereto over a period of about 12 minutes with a syringe. Thereafter, the resultant mixture was heated to about 40° C. and then agitated for 1 hour, thus obtaining a catalyst in the form of a hexane slurry containing a light-yellow, somewhat opaque, and fine powder.

Next, 350 ml of dehydrated hexane and 1/20 (=0.0980 g in terms of zinc atom) of the entirety of the catalyst slurry, as obtained by the above-mentioned operation, were placed in sequence into a 1-liter autoclave and then put under a pressure of 0.32 MPa with a nitrogen gas to perform a polymerization reaction at 20° C., while ethylene oxide was charged to the autoclave initially in an amount of about 15.0 g, and about 40 minutes later, intermittently charged to the autoclave using a continuous feed. This charging was carried out while the feed of ethylene oxide was regulated such that the internal pressure of the autoclave would increase by about 0.02 MPa in 5 minutes. The amount of ethylene oxide as charged was 118.3 g in total. After the charging of ethylene oxide had ended, aging was carried out for about 80 minutes, so that it was confirmed that the heat generation due to the polymerization had stopped. The polymerization time including the aging time was 6 hours. In addition, the conversion of ethylene oxide was 99.9%.

EXAMPLE 4

First, 400 ml of dehydrated hexane and 1/40 (=0.0490 g in terms of zinc atom) of the entirety of the catalyst slurry, as obtained in Example 3, were placed in sequence into a 1-liter autoclave and then put under a pressure of 0.32 MPa with a nitrogen gas to perform a polymerization reaction at 20° C., while ethylene oxide was charged to the autoclave initially in an amount of about 15.6 g, and about 30 minutes later, intermittently charged to the autoclave using a continuous feed. This charging was carried out while the feed of ethylene oxide was regulated such that the internal pressure of the autoclave would increase by about 0.02 MPa in 5 minutes. The amount of ethylene oxide as charged was 126.0 g in total. After the charging of ethylene oxide had ended, aging was carried out for about 180 minutes, so that it was confirmed that the heat generation due to the polymerization had stopped. The polymerization time including the aging time was 12 hours. In addition, the conversion of ethylene oxide was 95.2%.

Comparative Example 4

First, 17 ml of dehydrated hexane and 25 ml (about 18.37 g) of 20.28 weight % hexane solution of diethylzinc were put into a 500 ml flask as thoroughly dried and thoroughly subjected to nitrogen substitution. Then, 1.73 g of 1,4-butanediol (in the form of a solution with a mixed solvent of 11.0 g of dehydrated tetrahydrofuran and 5.11 ml of dehydrated hexane) was dropped thereto at room temperature over a period of about 50 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.6 g of hexane was dropped thereto over a period of about 28 minutes with a syringe. Thereafter, the resultant mixture was heated to about 40° C. and then agitated for 1 hour, thus obtaining a catalyst in the form of a hexane slurry containing a white powder.

Next, 350 ml of dehydrated hexane and 1/20 (=0.0986 g in terms of zinc atom) of the entirety of the catalyst slurry, as obtained by the above-mentioned operation, were placed in sequence into a 1-liter autoclave and then put under a pressure of 0.31 MPa with a nitrogen gas to perform a polymerization reaction at 20° C., while ethylene oxide was charged to the autoclave initially in an amount of about 15.3 g, and about 40 minutes later, intermittently charged to the autoclave using a continuous feed. This charging was carried out while the feed of ethylene oxide was regulated such that the internal pressure of the autoclave would increase by about 0.02 MPa in 5 minutes. The amount of ethylene oxide as charged was 120.7 g in total. After the charging of ethylene oxide had ended, aging was carried out for 176 minutes, so that it was confirmed that the heat generation due to the polymerization had stopped. The polymerization time including the aging time was 12 hours. In addition, the conversion of ethylene oxide was 99.1%.

As is evident from the results of Example 3 and Comparative Example 4 above, when the same amount of ethylene oxide is reacted using the same amount of catalyst, the use of the catalyst as prepared with the reversed micelle of Example 3 gives polyethylene oxide in about a half as long a time as that in Comparative Example 4.

Thus, it is clear that the productivity of the polyalkylene oxide per unit time is enhanced to about two times by using the catalyst as prepared with the reversed micelle.

Furthermore, as is evident from the results of Example 4 and Comparative Example 4 above, Example 4 gives polyethylene oxide with almost the same yield in the same reaction time using a half amount of catalyst when compared with Comparative Example 4. Thus, it is clear that the productivity of the polyalkylene oxide per unit amount of catalyst is enhanced to about two times by using the catalyst as prepared with the reversed micelle.

EXAMPLE 5

About 40 g of PELEX CS (chemical name: sodium dihexylsulfosuccinate: made by Kao Co., Ltd.) was put into a 100 ml separable flask (to which agitation vanes for high viscosity were then fitted) and then devolatilized under high vacuum of about 130 Pa at 180° C. for about 5 hours to reduce the water content. PELEX CS was a white wet powder before the devolatilization, but changed into a somewhat brown powder due to the devolatilization.

Next, 1.72 g of 1,4-butanediol, 25.15 g of PELEX CS, as dehydrated by the above devolatilization, and 182.75 g of toluene were put into a 500 ml flask as thoroughly dried and thoroughly subjected to nitrogen substitution. Then, the contents of the flask were stirred at room temperature for about 30 minutes to form a reversed micelle from 1,4-butanediol with the PELEX CS to dissolve 1,4-butanediol into toluene, thus obtaining a somewhat brown liquid.

While the above-mentioned somewhat brown solution was agitated at room temperature, 30 ml of hexane solution of diethylzinc of 1.0 mol/l was dropped thereto over a period of about 1 hour with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.52 g of toluene was dropped thereto over a period of 32 minutes with a syringe. Thereafter, the resultant mixture was heated to about 40° C. and then agitated for 1 hour, thus obtaining a catalyst in the form of a hexane slurry containing a somewhat brown, fine powder. The sedimentation time of the resultant organometallic fine particle was measured, but the particle sedimentated to a sedimentation volume of only 33 ml even in 233 hours.

Next, 250 ml of dehydrated hexane and 1/20 (=0.0980 g in terms of zinc atom) of the entirety of the catalyst slurry, as obtained by the above-mentioned operation, were placed in sequence into a 1-liter autoclave and then put under a pressure of 0.32 MPa with a nitrogen gas. Then, 53.7 g of ethylene oxide was charged from a continuous feed to the autoclave to perform a polymerization reaction at 20° C. The polymerization finished in about 120 minutes after the initiation of the charging of ethylene oxide. As a result, a polyethylene oxide was obtained with a conversion of about 100%.

EXAMPLE 6

Nonylphenol 6EO (adduct of 6 mol of ethylene oxide to nonylphenol) was dehydrated by drying with molecular sieves.

Next, 1.72 g of 1,4-butanediol, 24.66 g of nonylphenol 6EO, as dehydrated by drying above, and 95.0 g of toluene were put into a 500 ml flask as thoroughly dried and thoroughly subjected to nitrogen substitution. Then, the contents of the flask were stirred at room temperature for about 30 minutes to form a reversed micelle from 1,4 butanediol with the nonylphenol 6EO to dissolve 1,4-butanediol into toluene, thus obtaining a colorless transparent liquid.

While the above-mentioned transparent solution was agitated at room temperature, 30 ml of hexane solution of diethylzinc of 1.0 mol/l was dropped thereto over a period of 40 minutes with a syringe. The resultant mixture forms a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.5 g of toluene was dropped thereto over a period of 9 minutes with a syringe. Thereafter, the resultant mixture was heated to about 40° C. and then agitated for 2 hours, thus obtaining a catalyst in the form of a hexane slurry containing a somewhat opaque, fine powder. The sedimentation time of the resultant organometallic fine particle was 9.6 hours.

Next, 250 ml of dehydrated hexane and 1/20 (=0.0980 g in terms of zinc atom) of the entirety of the catalyst slurry, as obtained by the above-mentioned operation, were placed in sequence into a 1-liter autoclav and then put under a pressure of 0.33 MPa with a nitrogen gas. Then, 48.9 g of ethylene oxide was charged from a continuous feed to the autoclave to perform a polymerization reaction at 20° C. The polymerization finished in 4 hours after the initiation of the charging of ethylene oxide. As a result, a polyethylene oxide was obtained with a conversion of about 100%.

EXAMPLE 7

Aerosol OT-100 (chemical name: sodium dioctylsulfosuccinate: made by MITSUI CYTEC LTD.) was dehydrated by devolatilization under vacuum in the same way as of Example 1. Next, 1.45 g of 1,3-propanediol, 20.00 of Aerosol OT-100, as dehydrated by the above devolatilization, and 98.47 g of toluene were put into a 500 ml flask as thoroughly dried and thoroughly subjected to nitrogen substitution. Then, the contents of the flask were stirred at room temperature for about 30 minutes to form a reversed micelle from 1,3-propanediol with the Aerosol OT-100 to dissolve 1,3-propanediol into toluene, thus obtaining a colorless transparent liquid.

While the above-mentioned colorless solution was agitated at room temperature, 30 ml of hexane solution of diethylzinc of 1.0 mol/l was dropped thereto over a period of about 24 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.5 g of toluene was dropped thereto over a period of about 17 minutes with a syringe. Thereafter, the resultant mixture was heated to about 40° C. and then agitated for 1 hour, thus obtaining a catalyst in the form of a hexane slurry containing a light-yellow, somewhat opaque, and fine powder. The sedimentation time of the resultant organometallic fine particle was 4.5 hours.

Next, 250 ml of dehydrated hexane and 1/20 (=0.0980 g in terms of zinc atom) of the entirety of the catalyst slurry, as obtained by the above-mentioned operation, were placed in sequence into a 1-liter autoclave and then put under a pressure of 0.32 MPa with a nitrogen gas. Then, 48.9 g of ethylene oxide was charged from a continuous feed to the autoclave to perform a polymerization reaction at 20° C. The polymerization finished in 5 hours after the initiation of the charging of ethylene oxide. As a result, a polyethylene oxide was obtained with a conversion of about 98%.

EXAMPLE 8

Aerosol OT-100 (chemical name: sodium dioctylsulfosuccinate: made by MITSUI CYTEC LTD.) was dehydrated by devolatilization under vacuum in the same way as of Example 1. Next, 1.72 g of 1,4-butanediol, 24.9 of Aerosol OT-100, as dehydrated by the above devolatilization, and 99.0 g of toluene were put into a 500 ml flask as thoroughly dried and thoroughly subjected to nitrogen substitution. Then, the contents of the flask were stirred at room temperature for about 30 minutes to form a reversed micelle from 1,4-butanediol with the Aerosol OT-100 to dissolve 1,4-butanediol into toluene, thus obtaining a colorless transparent liquid.

While the above-mentioned colorless solution was agitated at room temperature, 30 ml of hexane solution of diethylzinc of 1.0 mol/l was dropped thereto over a period of about 29 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 1.37 g of ethanol and 12.5 g of toluene was dropped thereto over a period of about 15 minutes with a syringe. Thereafter, the resultant mixture was heated to about 40° C. and then agitated for 1 hour, thus obtaining a catalyst in the form of a hexane slurry containing a light-yellow, somewhat opaque, and fine powder. The sedimentation time of the resultant organometallic fine particle was 8 hours.

Next, 250 ml of dehydrated hexane and 1/20 (=0.0980 g in terms of zinc atom) of the entirety of the catalyst slurry, as obtained by the above-mentioned operation, were placed in sequence into a 1-liter autoclave and then put under a pressure of 0.33 MPa with a nitrogen gas. Then, 49.5 g of ethylene oxide was charged from a continuous feed to the autoclave to perform a polymerization reaction at 20° C. The polymerization finished in 4.5 hours after the initiation of the charging of ethylene oxide. As a result, a polyethylene oxide was obtained with a conversion of about 98%.

Comparative Example 5

Next, 250 ml of dehydrated hexane and 1/20 (=0.0980 g in terms of zinc atom) of the entirety of the catalyst slurry, as obtained in Comparative Example 3, were placed in sequence into a 1-liter autoclave and then put under a pressure of 0.33 MPa with a nitrogen gas. Then, 50.2 g of ethylene oxide was charged from a continuous feed to the autoclave to perform a polymerization reaction at 20° C. The polymerization finished in 7.5 hours after the initiation of the heat generation. As a result, a polyethylene oxide was obtained with a conversion of about 99%.

As is evident from the results of the polymerization using the same amount of catalyst in terms of zinc atom in Examples 5 to 8 and Comparative Example 5 above, the polymerization ends in a shorter time in Examples 5 to 8 (in which an organometallic fine particle is synthesized by micelle formation to be utilized as the catalyst for polymerization) than in Comparative Example 5.

EXAMPLE 9

Aerosol OT-100 (chemical name: sodium dioctylsulfosuccinate: made by MITSUI CYTEC LTD.) was dehydrated by devolatilization under vacuum in the same way as of Example 1. Next, 1.18 g of ethylene glycol, 20.00 of Aerosol OT-100, as dehydrated by the above devolatilization, and 92.2 g of toluene were put into a 500 ml flask as thoroughly dried and thoroughly subjected to nitrogen substitution. Then, the contents of the flask were stirred at room temperature for about 30 minutes to form a reversed micelle from ethylene glycol with the Aerosol OT-100 to dissolve ethylene glycol into toluene, thus obtaining a colorless transparent liquid.

While the above-mentioned colorless solution was agitated at room temperature, 30 ml of hexane solution of diethylzinc of 1.0 mol/l was dropped thereto over a period of about 32 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.5 g of toluene was dropped thereto over a period of about 25 minutes with a syringe. Thereafter, the resultant mixture was heated to about 40° C. and then agitated for 1 hour, thus obtaining a catalyst in the form of a hexane slurry containing a light-yellow, somewhat opaque, and fine powder. The sedimentation time of the resultant organometallic fine particle was 19.5 hours.

EXAMPLE 10

Aerosol OT-100 (chemical name: sodium dioctylsulfosuccinate: made by MITSUI CYTEC LTD.) was dehydrated by devolatilization under vacuum in the same way as of Example 1. Next, 0.34 g of water, 5.14 of Aerosol OT-100, as dehydrated by the above devolatilization, and 95.39 g of toluene were put into a 500 ml flask as thoroughly dried and thoroughly subjected to nitrogen substitution. Then, the contents of the flask were stirred at room temperature for about 30 minutes to form a reversed micelle from water with the Aerosol OT-100 to dissolve water into toluene, thus obtaining a colorless transparent liquid.

While the above-mentioned colorless solution was agitated at room temperature, 30 ml of hexane solution of diethylzinc of 1.0 mol/l was dropped thereto over a period of about 12 minutes with a syringe. The resultant mixture formed a milky dispersion while generating a gas. After the dropping had finished, the resultant dispersion was agitated for about 1 hour at room temperature and then for about 1 hour at 50° C. The dispersion was cooled to room temperature, and a mixed solution of 0.95 g of methanol and 12.5 g of toluene was dropped thereto over a period of about 12 minutes with a syringe. Thereafter, the resultant mixture was heated to about 40° C. and then agitated for 2 hours, thus obtaining a catalyst in the form of a hexane slurry containing a light-yellow, somewhat opaque, and fine powder. The sedimentation time of the resultant organometallic fine particle was 2.5 hours.

From the comparison between sedimentation velocities of the organometallic fine particles, it is clear that the sedimentation velocity is much slower in Examples 1 and 5 to 10 than in Comparative Examples 1 and 2.

In addition, although the nonionic surfactant is used both in Example 6 and Comparative Example 2, the sedimentation needs a longer time in Example 6 than in Comparative Example 2. The polyol in the reaction field is finely dispersed by solubilization in Example 6, but by emulsification in Comparative Example 2. Because the solubilization more effectively serves to enhance the degree of the fine dispersion than the emulsification, it is natural that the solubilization gives a finer organometallic particle and more decelerates the sedimentation velocity than the emulsification.

Incidentally at last, when the polyethylene oxides as obtained in Comparative Examples 1 to 5 were filtrated, crackle was made, wherein the crackle is heard when a sweater is taken off in the well dry air on a cold day in winter.

In addition, a plenty of polyethylene oxide, resultant from the polymerization, attached to the wall of the reaction vessel of the autoclave in Comparative Examples 1 to 5.

On the other hand, when the polyethylene oxides as obtained in Examples 1 to 8 were filtrated, no crackle was made, wherein the crackle is heard when a sweater is taken off.

In addition, none of the polyethylene oxide, resultant from the polymerization, attached to the wall of the reaction vessel of the autoclave in Examples 1 to 8.

Thus, it is clear that if the present invention organometallic fine particle is used as the catalyst for polymerization, the electrification due to static electricity is effectively prevented.

INDUSTRIAL APPLICATION

The following effects are obtained in the present invention.

1. The present invention enables easy synthesis of the organometallic fine particle.
2. If the organometallic fine particle as obtained in the present invention is used as the catalyst for polymerization, the polymerization reaction rate of ionic-polymerizable monomers mainly including an alkyl oxide can be accelerated.

What is claimed is:

1. A production process for an organometallic fine particle, comprising the step of reacting an organometallic compound and a compound (I) in the presence of an ionic surfactant solubilizing agent in a micelle as a reaction field, wherein the compound (I) is at least one member selected from the group consisting of water and active-hydrogen-containing compounds which have one or more carbon atoms, and wherein the organometallic compound is shown by the following general formula (1):

$$R_xM \qquad (1)$$

wherein: R is a hydrocarbon group having one or more carbon atoms;

M is a metal that shows Pauling's electronegativity of 0.5–3.0;

x is the valence of M.

2. A process according to claim 1, further comprising the step of forming the micelle in an inactive medium.

3. A process according to claim 1, wherein the organometallic compound is at least one member selected from the group consisting of alkylzincs, alkylaluminums, alkylmagnesiums, and alkylcalciums.

4. A process according to claim 1, being characterized in that the compound (I) is a polyol.

5. A process according to claim 4, wherein the compound (I) is an aliphatic polyol having 2~6 carbon atoms.

6. A process according to claim 4, wherein a polyol and a monohydric alcohol are used as the compound (I).

7. An organometallic fine particle, comprising a structural unit of the general formula (2) below:

(—M—O—Y—O—)            (2)

wherein: Y is a hydrocarbon group having one or more carbon atoms;

M is a metal that shows Pauling's electronegativity of 0.5–3.0;

with the particle being characterized by having a total content of silica, magnesia, and alumina of 2 weight % or less and by displaying a sedimentation velocity of 1 hour or more.

8. An organometallic fine particle according to claim 7, having an ionic surfactant content of 0.01 weight % or more.

9. A catalyst for polymerization, comprising the organometallic fine particle as recited in claim 7.

10. A catalyst dispersion for polymerization, comprising the catalyst for polymerization as recited in claim 9 and a solvent, wherein the catalyst is dispersed in the solvent.

11. A production process for a (poly)alkylene oxide, comprising the step of ring-opening polymerization of a cyclic ether in the presence of the catalyst for polymerization as recited in claim 9, thus producing the (poly)alkylene oxide.

* * * * *